United States Patent [19]
Johnson et al.

[11] Patent Number: 5,473,102
[45] Date of Patent: Dec. 5, 1995

[54] PROCESS FOR RECOVERY OF AROMATIC ACID AND DIHYDRIC ALCOHOL FROM WASTE POLYESTER RESINS

[75] Inventors: Floyd Johnson, Warrenville; David L. Sikkenga, Wheaton; Kalpana Danawala, Niles; Bruce I. Rosen, Morton Grove, all of Ill.

[73] Assignee: Amoco Corporation, Chicago, Ill.

[21] Appl. No.: 318,228

[22] Filed: Oct. 5, 1994

[51] Int. Cl.$^6$ .................................................. C07C 67/60
[52] U.S. Cl. ........................ 562/483; 562/485; 568/868
[58] Field of Search .................................. 562/483, 485; 568/868

[56]     References Cited

U.S. PATENT DOCUMENTS

| | | | |
|---|---|---|---|
| 3,526,658 | 9/1970 | Bryant | 260/525 |
| 4,355,175 | 10/1982 | Pusztaszeri | 562/483 |
| 4,605,762 | 8/1986 | Mandoki | 562/483 |
| 4,620,032 | 10/1986 | Doerr | 562/483 |
| 5,051,528 | 9/1991 | Naujokas et al. | 560/78 |

OTHER PUBLICATIONS

H. S. Bryant et al., "Mobil's Process for TPA," *Chemical Engineer Progress* (vol. 67, No. 9), Sep. 1971, pp. 69–75.

Primary Examiner—Jos' G. Dees
Assistant Examiner—Samuel Barts
Attorney, Agent, or Firm—Thomas E. Nemo; Wallace L. Oliver

[57]     ABSTRACT

Processes are disclosed for recovery and purification of dibasic aromatic acids from waste polyester film, fiber, bottles, manufacturing residues, and other manufactured articles. The processes comprises: depolymerization of polyester resin in a molten polyester resin containing solvent with superheated stem, and vaporization of the aromatic carboxylic acid and other volatile products of hydrolysis to obtain a vaporized mixture containing aromatic acid, dihydric alcohol, other volatile products of hydrolysis, and water. This vapor mixture is, advantageously, substantially free of less volatile and non-volatile impurities including metals, and many colored and color causing compounds, which are, typically, found in post-consumer polyester resins.

Crude acid is, optionally, purified by hydrogenated in an aqueous solution at elevated temperatures and pressures in the presence of hydrogen and an insoluble metal-containing catalyst, which is thereupon separated from the aqueous solution, and purified dibasic aromatic acid recovered by crystallization and mechanical separation from the aqueous solution. Purified terephthalic acid has, typically, a L*-value in a rage of from about 95 to about 100, an a*-value in a rage of from about −1 to about +1, and a b*-value in a range of from about 0.5 to about 2.

20 Claims, 1 Drawing Sheet

PROCESS FOR RECOVERY OF AROMATIC ACID AND DIHYDRIC ALCOHOL FROM WASTE POLYESTER RESINS

FIELD OF THE INVENTION

The field of this invention relates to preparation of aromatic acid and/or dihydric alcohol from waste polyester resins by processes including depolymerization of polyester resin comprising repeating units of aromatic acid residue and repeating units of dihydric alcohol residue linked by ester bonds, which processes involve hydrolysis of the ester bonds and vaporization of the aromatic carboxylic acid and other volatile products of hydrolysis. More particularly, this invention concerns a recovery process comprising: depolymerizing polyester resin in a molten polyester resin containing solvent with superheated steam to obtain a vaporized mixture containing aromatic acid, dihydric alcohol, other volatile products of hydrolysis, and water. This vapor mixture is, advantageously, substantially free of less volatile and non-volatile impurities including metals, and many colored and color causing compounds, which are, typically, found in post-consumer polyester resins.

In one aspect this invention relates to processes for manufacture of terephthalic acid which processes involve depolymerizing polyethylene terephthalate resin with superheated stem in a pool of molten resins to obtain a mixture of vapors containing ethylene glycol, terephthalic acid, and volatile products from the hydrolysis of waste polyethylene terephthalate resin. Processes, for example, in which both an ethylene glycol product and a terephthalic acid product are recovered by an initial partial or total condensation of their vapors, separation of precipitated terephthalic acid product from a gas phase and/or crystallized terephthalic acid product from liquid products, and fractionation of acid-free products to obtain dehydrated ethylene glycol product free of intermediate products from the hydrolysis, such as, mono(2-hydroxyethyl)-terephthalate.

In another aspect this invention relates to processes for manufacture 2,6-naphthalene dicarboxylic acid which processes include both recovering 2,6-naphthalene dicarboxylic acid and ethylene glycol. Waste poly(ethylene-2,6-naphthalate) resins are, according to this invention, depolymerized with superheated stem in a pool of molten resins to obtain a mixture of vapors containing ethylene glycol, 2,6-naphthalene dicarboxylic acid, and volatile products from the hydrolysis of waste poly(ethylene-2,6-naphthalate) resin. Ethylene glycol product and 2,6-naphthalene dicarboxylic acid product are recovered by an initial partial or total condensation of their vapors, separation of precipitated 2,6-naphthalene dicarboxylic acid product from a gas phase and/or crystallized 2,6-naphthalene dicarboxylic acid product from liquid products, and fractionation of acid-free products to obtain dehydrated ethylene glycol product free of intermediate products from the hydrolysis.

BACKGROUND OF THE INVENTION

Aromatic dicarboxylic acids are well known starting materials for making polyester resins, which polyester resins are used widely as principal polymers for polyester fibers, polyester films, and resins for bottles and like containers. For a polyester resin to have properties required in many of these uses, the polyester resin must be made from a polymer grade or "purified" aromatic acid, such as purified terephthalic acid.

Purified terephthalic acid is derived from relatively less pure, technical grade or "crude" terephthalic acid by purification of the latter utilizing hydrogen and a noble metal catalysts as described in U.S. Pat. No. 3,584,039 to Meyer. In the purification process, impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts various color bodies present in the relatively impure terephthalic acid to colorless products. Another related purification-by-hydrogenation process of aromatic polycarboxylic acids produced by liquid phase catalyst oxidation of polyalkyl aromatic hydrocarbons is described in U.S. Pat. No. 4,405,809 to Stech et al.

Depolymerization of polyethylene terephthalate by hydrolysis at a high temperature and pressure in the absence of a base or acid, or a catalyst, is known, see for example, U.S. Pat. No. 4,521,556; U.S. Pat. No. 4,587,502; U.S. Pat. No. 4,605,762; GB. Patent No 2,123,403; U.S. Pat. No. 4,578,510; U.S. Pat. No. 4,620,032; U.S. Pat. No 4,626,598; Japanese Patent No. 49020147; and Japanese Pat. No. 56118420. Depolymerization of polyethylene terephthalate by hydrolysis under conditions of neutral pH can, however, result in production of oligomeric co-products (U.S. Pat. No. 4,578,510); derivatives of terephthalic acid (Wolkma Chem., 13(2), 144–55); and/or cyclic trimers (Japanese Patent No. 56118420). Additionally, depolymerization product of waste polyethylene terephthalate in the form of bottles, film, fiber and other manufactured articles usually contain dyes and contaminants (U.S. Pat. No. 4,521,556; GB. Patent No 2,123,403; and Japanese Patent No. 49020147). Accordingly, although various processes are available for hydrolyzing polyethylene terephthalate waste, the purification of recovered terephthalic acid typically requires several process steps to remove dyes, pigments, and other impurities including inorganic compounds such as catalyst residues and organic compounds which can result from depolymizeration reactions.

U.S. Pat. No. 4,335,175, to Pusztaszeri, exemplifies some difficulties encountered in preparing a purified terephthalic acid from polyethylene terephthalate waste. Polyester scrap such as film (with or without silver), fabric, yarn, or bottles, was depolymerized at ambient temperatures with a mixture of concentrated sulfuric acid and water to form crude terephthalic acid. Pusztaszeri states that an alkaline solution, which can be dark brown or black in color, containing crude terephthalic acid resulting from the depolymerization, is filtered to obtain a clear liquid which many be light brown in color (if colored, it must be treated with activated charcoal and filtered from the charcoal). The resulting solution is then acidified with sulfuric acid to precipitate the terephthalic acid. Terephthalic acid is then recovered by filtration and washed.

In U.S. Pat. No. 5,051,528 to Naujokas and Ryan, a method is described for recovering ethylene glycol and forming dimethyl terephthalate from polyethylene terephthalate waste by dissolving the scrap in a solvent consisting of oligomers of the same monomers at atmospheric pressure and passing super-heated methanol through the solution at temperatures below 270° C. Dimethyl terephthalate and ethylene glycol are said to be carried out of the solution with the flow of super-heated methanol. Methanol is recovered overhead from the product vapor stream in a first distillation column. In a subsequent distillation column, dimethyl terephthalate and ethylene glycol are separated from a bottom effluent of the first distillation column. "However, aromatic carboxylic acids cannot be obtained directly by this method because of the use of super-heated methanol resulting in formation of dimethyl terephthalate.

In a later filed European Patent Application No 484 963 A2, in the name of Everette, a method is described for obtaining ethylene glycol vapor and forming dimethyl terephthalate vapor by treating polyester polymer with excess methanol vapors at a temperature above 230° C. The excess methanol is said to act as a carrier gas for the ethylene glycol vapor and dimethyl terephthalate vapor. At a pressure of 110 psig the reported yields of dimethyl terephthalate were, even with an excess of at least 3 moles of methanol for every mole of dimethyl terephthalate in the vapor, in a range downward from 88 based on PET content of the starting material. At lower pressures, lower yields were reported for this process. Again, aromatic carboxylic acids cannot be obtained directly by this method because of the use of excess methanol resulting in formation of dimethyl terephthalate.

Recently, in U.S. Pat. No. 5,095,145, to Rosen, a process is disclosed for preparing a purified terephthalic acid from waste polyethylene terephthalate. Scrap was depolymerized at temperatures of from about 221° C. to about 316° C. with water at pressures sufficient to maintain a liquid phase and, subsequent to cooling, a crude terephthalic acid filter cake was recovered from the resulting solution and washed. The cake was reslurried and dissolved in water. Thereupon, the solution obtained was catalytically hydrogenated at temperatures of from about 221° C. to about 316° C. at pressures sufficient to maintain a liquid phase for a period of up to 8 hours. Rosen states that pellets of green waste polyethylene terephthalate from waste green bottles were depolymerized by this process at 274° C. and samples of crude terephthalic acid filter cakes taken after 2 hours and a longer period. After filter cakes of terephthalic acid from green bottles were analyzed for color, $L^*$-values of 91.54 and 68.18, $a^*$-values of $-0.55$ and 1.22, and $b^*$-values of 5.22 and 15.88, respectively, were reported. In Example XII of U.S. Pat. No. 5,095,145 it is stated that hydrogenation of crude terephthalic acid from waste green polyethylene terephthalate required up to about 6 hours to reduce initial $b^*$-values greater than 2 but less than 10 to less than 2. The reported $L^*$-value, however, increased to over 95 and $a^*$-values also increased, but remained negative.

Regardless of the methods of depolymerization and purification of resulting terephthalic acid, the variable nature of crude terephthalic acid obtained from depolymerization of polyethylene terephthalate waste from many sources and the variable nature of impurities resulting therefrom and contained in the crude terephthalic acid, the process control and thus quality assurance of the purified terephthalic acid, has been made difficult and costly. Because of this lack of quality assurance and its cost relative to that of virgin purified terephthalic acid, purified terephthalic acid from polyethylene terephthalate waste has not been considered as a viable economic replacement for fiber grade virgin purified terephthalic acid prepared from para-xylene.

It is therefore a general object of the present invention to provide an improved method which overcomes the aforesaid problem of prior art methods, for recovery of aromatic acid from polyester resin which has been used for polyester fibers, polyester films, and resins in bottles and like containers.

More particularly, it is an object of the present invention to provide an improved method for recovery from polyester resins aromatic acid sufficiently free of undesired impurities so that the acid can be used to make polyester resins which have good color and other properties needed in manufacture of commercial articles.

Other objects and advantages of the invention will become apparent upon reading the following detailed description and appended claims.

SUMMARY OF THE INVENTION

Economical processes are disclosed for recovering dibasic aromatic acid and/or dihydric alcohol from polyester resin comprising repeating units of dibasic aromatic acid residue and repeating units of dihydric alcohol residue linked by ester bonds. Processes according to this invention include, broadly, preparation of aromatic acid vapors and dihydric alcohol vapors by treating polyester resins with superheated steam in a hydrolysis zone and continuously removing therefrom a mixture of vapors containing aromatic acid, dihydric alcohol, other volatile products of hydrolysis, and water.

More particularly, recovery processes according to this invention comprise: depolymerizing polyester resin in a pool containing molten polyester resin with excess superheated stem and continuously removing a mixture of vapors containing aromatic acid, dihydric alcohol, other volatile products of hydrolysis, and water from the pool. This vapor mixture is substantially free of less volatile and non-volatile impurities including metals, colored and color causing compounds, which are, typically, found in post-consumer polyester resins. Generally, these processes also include separating a solid aromatic acid product from the vapor mixture by condensation and/or crystallization. The dibasic aromatic acid is, preferably, at least one member of the group consisting of isophthalic acid, terephthalic acid, and 2,6-naphthalene dicarboxylic acid.

Where desired, a dehydrated dihydric alcohol product is recovered by fractional distillation of effluent of the separation of solid aromatic acid product. At least a portion of the water vapor and/or the lower boiling compounds from the fractional distillation are, advantageously, recycled to the depolymerization.

In one aspect of this invention, a dibasic aromatic acid is produced by a process which comprises: depolymerizing polyester resin in a molten polyester resin containing solvent under conditions suitable for hydrolysis of ester bonds to form a reaction mixture containing aromatic acid, dihydric alcohol, impurities and other components of the resin; vaporizing from the reaction mixture the aromatic carboxylic acid, dihydric alcohol, and other volatile products of hydrolysis, such as mono(2-hydroxyethyl)terephthalate (MHET), bis(2-hydroxyethyl)-terephthalate (BHET), and like organic compounds, to obtain an effluent of depolymerization containing aromatic acid, dihydric alcohol, and other volatile products of hydrolysis; and separating from the effluent of depolymerization a solid product of crude dibasic aromatic acid substantially free of dihydric alcohol, but containing organic impurities, to form a residue containing dihydric alcohol. Both the depolymerizing of polyester resin and the vaporization of the aromatic carboxylic acid and other volatile products of hydrolysis, are, generally, carried out together in one or more reaction zones.

Sources of waste polyester resins made from different aromatic acids are suitable, even without initial sorting. Processes according to this invention are particularly suitable for recovery of at least one member of the group consisting of isophthalic acid, terephthalic acid, and 2,6-naphthalene dicarboxylic acid. Polyethylene terephthalate and poly(ethylene-2,6-naphtalate) resins are, preferably, treated with excess superheated stem at temperatures above about 240° C., preferably, temperatures are in a range of from about 250° C. to about 450° C. and at pressures sufficient to maintain a molten phase. Generally, pressures in the reaction zones are below about 15 atmospheres, typically, pressures are in a range upward from about 0.1 atmosphere to about 15 atmospheres, and advantageously, pressures are in a range upward from about 1 atmosphere to about 10 atmospheres.

Where alcohol product of higher purity is desired, a process for recovering dihydric alcohol according to this invention, further comprises: fractionating at least a portion of a residue resulting from the separation of aromatic acid from the vaporized products of depolymerization to obtain a dihydric alcohol product substantially free of lower boiling compounds. Generally, fractionation of the residue containing the desired alcohol is by means of continuous distillation to obtain an overhead fraction of lower boiling compounds, such as water, a dehydrated alcohol product, and a bottom fraction containing lower boiling compounds. At least a portion of the bottom fraction is, advantageously, recycled to one or more of the reaction zones where the depolymerization of polyester resin is carried out in the presence of the lower boiling compounds.

Where aromatic acid product of higher purity is desired, processes for recovering dibasic aromatic acid from polyester resin according to this invention, further comprises: reducing at least a portion of the organic impurities in the crude dibasic aromatic acid in an aqueous solution at elevated temperatures and pressures and in the presence of hydrogen and at least one insoluble Group VIII noble metal-containing catalyst; separating the solid noble metal-containing catalyst from the aqueous solution; and crystallizing and separating purified dibasic aromatic acid from the aqueous solution while maintaining the temperature in a range of from about 50° C. to about 150° C. The resulting purified terephthalic acid has a L*value in a range of from about 95 to about 100, an a*-value in a range of from about −1 to about +1, and a b*-value in a range of from about 0.5 to about 2.

Fiber-grade terephthalic acid is, generally, obtained using a hydrogenation catalyst in which the noble metal is at least one member of the group consisting of palladium and rhodium. Purified terephthalic acid produced from waste polyethylene terephthalate according to this invention has a total metals content of less than about 400 ppm and, preferably, less than 100 ppm.

When the insoluble metal-containing catalyst has a palladium containing component on a carbon support, terephthalic acid produced from waste polyethylene terephthalate according to this invention has a total metals content of less than 10 ppm, and color measured by a L*-value greater than about 95, preferably in a range of from about 95 to about 100, an a*-value greater than about −1.5, preferably in a range of from about −1 to about +1, and a b*-value less than about 2, preferably in a range of from about 0.5 to about 2.

In another aspect this invention is a process for recovering terephthalic acid from polyethylene terephthalate resin containing repeating units of terephthalic acid residue and repeating units of ethylene glycol residue linked by ester bonds which process comprises: depolymerizing polyethylene terephthalate resin with excess superheated steam in a pool containing molten resins under conditions suitable for hydrolysis of ester bonds to form a reaction mixture containing terephthalic acid, ethylene glycol, impurities and other components of the resins; vaporizing from the reaction mixture the terephthalic acid, ethylene glycol, and other volatile products of hydrolysis with excess superheated steam to obtain an effluent of depolymerization comprising terephthalic acid, ethylene glycol, other volatile products of hydrolysis, and water in an mount of at least about 2 moles of water per mole of terephthalic acid in the effluent of depolymerization; separating from the effluent of depolymerization a solid product of crude terephthalic acid substantially free of ethylene glycol, but containing organic impurities, to form a residue containing ethylene glycol; and fractionating at least a portion of the residue to obtain dehydrated ethylene glycol substantially free of lower boiling compounds, and a fraction containing lower boiling compounds.

Processes for recovering terephthalic acid from polyethylene terephthalate resin, optionally, further comprise: reducing at least a portion of the organic impurities in the crude terephthalic acid in an aqueous solution at elevated temperatures and pressures and in the presence of hydrogen and an insoluble catalyst containing a palladium component on a carbon support; separating the insoluble catalyst from the aqueous solution; and crystallizing and separating purified terephthalic acid from the aqueous solution while maintaining the temperature in a range of from about 50° C. to about 150° C. Advantageously, resulting purified terephthalic acid has a L*-value in a range of from about 95 to about 100, an a*-value in a range of from about −1 to about +1, and a b*-value in a range of from about 0.5 to about 2.

In another aspect of this invention, 2,6-naphthalene dicarboxylic acid is recovered from poly(ethylene-2,6-naphthalate) resin in process comprising: depolymerizing from poly(ethylene-2,6-naphthalate) resin with excess superheated stem in a pool containing molten resins under conditions suitable for hydrolysis of ester bonds to form a reaction mixture containing 2,6-naphthalene dicarboxylic acid, ethylene glycol, impurities and other components of the resins; vaporizing from the reaction mixture the 2,6-naphthalene dicarboxylic acid, ethylene glycol, and other volatile products of hydrolysis with excess superheated stem to obtain an effluent of depolymerization comprising 2,6-naphthalene dicarboxylic acid, ethylene glycol, other volatile products of hydrolysis, and water in an mount of at least about 2 moles of water per mole of 2,6-naphthalene dicarboxylic acid in the effluent of depolymerization; separating from the effluent of depolymerization a solid product of crude 2,6-naphthalene dicarboxylic acid substantially free of ethylene glycol, but containing organic impurities, to form a residue containing ethylene glycol; and fractionating at least a portion of the residue to obtain dehydrated ethylene glycol substantially free of lower boiling compounds.

Preferred processes for obtaining purified 2,6-naphthalene dicarboxylic acid further comprises: reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst; separating the solid noble metal-containing catalyst from the aqueous solution; and crystallizing and separating from the aqueous solution purified 2,6-naphthalene dicarboxylic acid while maintaining the temperature in a range of from about 25° C. to about 250° C. Advantageously, purified 2,6-naphthalene dicarboxylic acid has an optical density in a range from about 0 to about 5, an ash content of less 500 ppm, and/or a metals content of less than 200 ppm.

BRIEF DESCRIPTION OF THE INVENTION

Suitable sources of polyester resin for use in this invention include polyester fibers, polyester films, and manufactured articles such as bottles and like containers. Resins are, generally, made up of structural units which are repeated many times to obtain high molecular weight and other desired properties. In polyester resins repeating structural units are made up of dibasic acid residue and, typically, dihydric alcohol residue linked by ester bonds, i.e., units in which acidic hydrogen atoms of a dicarboxylic acid molecule are replaced by a hydrocarbon group. In preferred polyester resin for use in this invention, the repeating structural units are, generally, made up of aromatic acid residue, preferably, from aromatic acids. Carboxyl groups in preferred aromatic acids are either attached directly to an independent benzene ring or to benzene rings of a condensed ring system such as naphthalene, in which two benzene rings have two carbon atoms in common or anthracene in which three rings are similarly connected so that the rings are not independent.

Suitable polyester resins for use in methods producing aromatic acid according to this invention have repeating structural units containing residues of any dicarboxylic acid which can be formed from a corresponding methyl substituted aromatic compound by liquid-phase oxidation with an oxygen-containing gas in the presence of an oxidation catalyst at elevated pressures and temperatures. Polyester resins, for example, which have repeating structural units containing residues of isophthalic acid, terephthalic acid, naphthalene dicarboxylic acid, 4,4'-oxybis(benzoic acid), 5-tert-butyl-1,3-benzene dicarboxylic acid and the like. Particularly useful are polyester resins which have repeating structural units containing residues of terephthalic acid or 2,6-naphthalene dicarboxylic acid.

An essential element of processes of this invention is that a portion of undesired impurities present with aromatic acid obtained by depolymerization of polyesters (impurities consisting of metals, metal oxides, silicas, aluminas, and/or other plastics typically found in post-consumer polyester resin of waste) which impurities remain in the liquid-phase and are separate from the gas-phase containing the desired aromatic acid and dihydric alcohol having an improved purity.

Processes according to this invention are advantageous in that the recovered aromatic acid and dihydric alcohol are freed of many components and impurities present in commercially available sources of post-consumer wastes. Thus, the make up of polyester waste is not critical to the recovery process and the inventive method is very satisfactory. Suitable sources of polyester include, for example, flaked and/or ground polyester bottles along with all their components, such as, polyethylene bottom cups, labels, bottle caps, and bottle contents; photographic and other sources of film scrap, and scrap containing other polymers including acetate resins, polyvinyl chloride and the like. Processes according to this invention are well suited to process wastes containing blends of polyester fibers with other fibers, such as cotton, polyester that is metallized, polyester that is died, polyester that is pigmented, and/or polyester that is mixed witch other plastics.

Processes according to this invention are particularly useful in recovery of aromatic acid from polyester waste containing metal-organic components used to color polyester articles, because of the excellent color obtained in polyesters made from the recovered aromatic acid. Copper containing components of polyester waste, for example, copper phthalocyanine ($C_{32}H_{16}CuN_8$) and compounds derived therefrom, cause impurities which are difficult to remove from aromatic acid. Copper levels in aromatic acid produced by processes of this invention are less than 5 ppm, and preferably less than 1 ppm.

In preparation of comminuted polyester resin, polyethylene terephthalate waste is, for example, subjected to the action of a granulator, or a crusher, or a grinding machine to reduce the waste material to a suitable particle size which can be as large as about one-half inch, or about 2 cm, in maximum length and about one-eight inch, or about 0.5 cm, in thickness.

Superheated steam passing though the reaction zones provides; heat required to melt and/or maintain a pool of molten polyester resin containing solvent and carry out the depolymerization, water for the hydrolysis, heat to vaporize volatile products of hydrolysis and acts as a carrier gas to continuously sweep vapors from the reaction zones. As result of depolymerization, the pool of molten polyester resin will contain oligomers of the same monomers as that of the polymer, i.e., ethylene glycol and isophthalic acid, terephthalic acid and/or 2,6-naphthalene dicarboxylic acid. Excess stem can act as a carrier gas to continuously sweep vapors from the reaction zones at levels as low as that required to obtain at least about 2 moles of water per mole of aromatic acid in the mixture of vapors. It is preferred that the vapor leaving the reaction zones contain at least about 4 moles of water per mole of aromatic acid, and mole ratios as high as 150 moles of water per mole of aromatic acid are useful.

The purification step of the instant invention can be carried out in a batch mode as well as a continuous mode. For commercial scale purification of terephthalic acid a continuous mode is preferred. In any event, however, a*-value and b*-value of crude terephthalic acid and purified terephthalic acid are monitored so as to obtain a desired color lever of final product, a fiber-grade terephthalic acid.

Terephthalic acid concentration in the solution to be purified by hydrogenation can vary over a relatively wide range. Concentration can be as low as about 5 percent by weight or as high as about 35 percent by weight, based on the weight of the solution. Preferably, the solution concentration of terephthalic acid is in a range of from about 10 to about 30 percent by weight.

Pressure employed in the purification step depends primarily upon the temperature employed therein. Inasmuch as the temperatures at which practical amounts of the impure terephthalic acid may be dissolved in an aforesaid solvent are substantially above the normal boiling point of the solvent, the process pressures are necessarily considerably above atmospheric pressure to maintain the aqueous solution in a liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and or nitrogen in the head space. Use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in a rage of about 200 to about 1,500 pounds per square inch gauge (psig), and usually is in a rage of about 900 psig to about 1,200 psig.

The reactor employed in the purification step can he operated in several modes. For example, a predetermined liquid level can be maintained in the reactor, and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative mounts of hydrogen and inert gas present in the admixture.

In yet another operating mode, the reactor can be filled with the terephthalic acid solution so as to provide no reactor vapor space, that is, the reactor can be operated as a hydraulically full system with dissolved hydrogen being fed to the reactor under flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in a range of from about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution.

In general, the mount of hydrogen supplied to the purification reactor under reaction conditions is, of course, sufficient to effect the desired hydrogenation.

As described in the aforementioned U.S. Pat. Nos. 3,584,039; 3,726,915; and 4,405,809, catalysts that are suitable for use in the aforesaid purification step are insoluble under the conditions employed therein and comprise at least one supported or unsupported Group VIII noble metal, whose class includes palladium, rhodium, ruthenium, osmium, iridium, and platinum. Preferably, the noble metal is at least one member of the group consisting of palladium and rhodium. Other catalysts effective for aqueous liquid-phase hydrogenation under the relatively mild hydrogenation conditions described herein above are listed in Kirk-Othmer, *Encyclopedia of Chemical Technology,* Wiley-Interscience, particularly in chapters on Hydrogenation and Catalysts. See also U.S. Pat. No. 2,070,770 to Amend and U.S. Pat. No. 2,105,664 to Lazier.

A preferred method for hydrogenation of crude 2,6-naphthalene dicarboxylic acid according to the present invention is the subject of U.S. Pat. No. 5,256,817 to Sikkenga and Hoover, the disclosure of which is incorporated herein by reference.

Preferably, the catalyst comprises a support. Preferred support materials include carbon and charcoal. Typically, the catalyst carrier is active carbon, usually that derived from coconut charcoal in the form of granules having a surface area of at least about 600 $m^2/g$ measured by the BET method using nitrogen. Other porous carbonaceous supports or substrates can, however, be used as long as the surface area requirements can be met. In addition to coconut charcoal, activated carbon derived from other plant or from animal sources can be utilized.

The noble metal component is present on the carrier at a concentration level in a range of from about 0.01 weight percent to about 2 weight percent, based on total weight of catalyst, i.e., metal plus active carbon carrier, and calculated as the elemental noble metal. Preferably, the catalyst metal loading is about 0.5 weight percent.

A typical catalyst of palladium on a support comprises from about 0.01 weight percent to about 2 weight percent of palladium, based on total weight of catalyst and calculated as elemental metal. The support or carrier for the palladium is porous and inert, and preferably is active carbon having a surface area of about 600 $m^2/g$ to about 1,500 $m^2/g$. Suitable supports for Pd/C hydrogenation catalysts are well-known and are described, inter alai, in U.S. Pat. No. 3,584,039 to Meyer.

A suitable palladium-on-carbon catalyst can be obtained, for example, from Engelhard Corporation, Newark, N.J., under the designation "Palladium on Activated Carbon Granules (Carbon Code CG-S)." Similarly, suitable rhodium-on-carbon catalysts can be obtained from Engelhard Corporation, under the designations "Rhodium on Activated Carbon Granules (carbon Code CG-5)" and "Rhodium on Activated Carbon Granules (carbon Code CG-21)." Both of these catalysts have a BET; $N_2$ surface area of about 1,000 $m^2/g$ and have a particle size of 4×8 mesh, U.S. Sieve Series. Other suitable rhodium-on-carbon catalysts of similar size and surface area are available from Johnson Matthey Inc., Seabrook, N.H., under the designation "11766 Rhodium, 1% on Stem Activated Carbon Granules, Anhydrous."

Space velocity reported as weight of crude terephthalic acid solution per weight of catalyst per hour in the purification step is in a range of from about 5 $hours^{-1}$ to about 25 $hours^{-1}$, preferably from about 10 $hours^{-1}$ to about 15 $hours^{-1}$. Residence time of the solution in the catalyst bed varies, depending upon activity of catalysts present.

The color level of crude terephthalic acid, purified terephthalic acid product, and polyethylene terephthalate can be monitored or evaluated directly or indirectly, as described herein below. Partial pressure of hydrogen in the reactor can be adjusted to compensate for any detected impermissible deviation of the purified terephthalic acid from the desired color level. Adjustment can be made by the procedure taught in U.S. Pat. No. 4,782,181, which is incorporated herein by reference.

In one aspect, color level of crude terephthalic acid, purified terephthalic acid product, and polyethylene terephthalate can be ascertained by measuring its b*-value on the Hunter Color Scale as described in Hunter, The Measurement of Appearance, Chapter 8, pp. 103 to 132, John Wiley & Sons, N.Y. (1975), and in Wyszecki et al., Color Science Concepts and Methods, Quantitative Data and Formulae, 2d Ed., pp. 166 to 168, John Wiley & Sons, N.Y. (1982).

More specifically, b*-values of crude terephthalic acid, purified terephthalic acid product, and polyethylene terephthalate can be determined using, for example, a Diano Match Scan Spectrophotometer as follows. A sample of solid product is pressed into a pellet having a thickness of about 0.25 inch and a diameter of about 1 inch. The pellet is then irradiated with white light that has been UV-filtered. The spectrum of visible light reflected from the sample is determined and tristimulus values (X, Y, and Z) are computed using the CIE Standard Observer functions. Using a weighted-ordinate method, tristimulus values are obtained from the following equations:

$$X = \sum_{400}^{700} R\lambda\, x\lambda,\ Y = \sum_{400}^{700} R\lambda\, y\lambda,\ Z = \sum_{400}^{700} R\lambda\, z\lambda,$$

where $R\lambda$ is the percent reflectance of the pellet at wavelength $\lambda$ and $x\lambda$, $y\lambda$, and $z\lambda$ are Standard Observer functions at wavelength 1 for CIE Illuminated D65. Tristimulus values X, Y, and Z, identify the color of the pellet in terms of a mixture of primary colors that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100\, Y/Y_0)^{1/3} - 16$$

$$a^* = 500[(X/X_0)^{1/3} - (Y/Y_0)^{1/3}]$$

$$b^* = 500[(Y/Y_0)^{1/3} - (Z/Z_0)^{1/3}]$$

The L* value is a measure of the luminosity or whiteness of an object where a L* value of 100 is pure white, a L* value of 0 is black, and values in a rage 0<L*<100 are gray. The L* value is strictly a function of tristimulus Y-value. The b*-value is a measure of a yellowness-blueness attribute where positive b*-values represent yellow appearance and negative b*-values represent blue appearance. The b*-value is a function of both tristimulus values Y and Z.

Alternatively, by the aforesaid indirect method, the color level, e.g., b*-value, of purified terephthalic acid product can be correlated with optical density of (OD) of incoming feed and utilized to adjust the partial pressure of hydrogen in the reactor. Typically, optical density values can be determined using a spectrophotometer and a light beam having wavelength of 340 nanometers (nm/or millimicrons (mu), correlated with b*-value of purified terephthalic acid product at specific partial pressure of hydrogen for a given catalyst and then used to adjust the partial pressure of hydrogen during a particular process run so as to produce purified product having the desired b*-value.

It has been found that a 0.1 unit deviation in b*-value of purified terephthalic acid product can be compensated by an adjustment in partial pressure of hydrogen in the reactor of as low as about 5 psi to as high as about 60 psi depending upon activity of catalyst employed. If a fresh, relatively high activity catalyst is used, an initial adjustment in partial pressure of hydrogen required for a 0.1 unit deviation in b*-value is, usually, in a range of from about 5 psi to about 7.5 psi. As catalyst stabilizes, however, the adjustment in partial pressure of hydrogen required for a 0.1 unit deviation in b*-value is, usually, in a rage of from about 40 psi to about 50 psi.

It has been found that a 0.1 unit change in optical density at 340 nm ($OD_{340}$) of feed solution correlates with about 0.05 unit change in b*-value of purified terephthalic acid product which is obtained from that particular feed solution. Thus, a 0.1 unit change in $OD_{340}$-value of the feed solution can, usually, be compensated by an adjustment in partial pressure of hydrogen in the reactor in a range of from about 2.5 psi to about 4 psi for a fresh, relatively high activity catalyst. As activity of a catalyst stabilizes during use, however, a 0.1 unit change in $OD_{340}$-value of the feed solution can, usually, be compensated by an adjustment in partial pressure of hydrogen in the reactor in a range of from about 20 psi to about 25 psi.

An overall relationship among b*-value, partial pressure of hydrogen in the reactor, and $OD_{340}$ can also be expressed as $$b^*\text{-value} \propto A\,(H_{2pp}) + C\,(OD_{340})$$

where $H_{2pp}$ designates partial pressure of hydrogen in the reactor expressed in psi, $OD_{340}$ is the optical density value of crude terephthalic acid feed solution of the reactor, A is a number in a range of from about 0.001 to about 0.03, and C is a number in a range of from about 0.4 to about 1.4.

Similarly, an overall relationship among b*-value, concentration of hydrogen in the reactor solution, and optical density at 340 nm can be expressed as $$b^*\text{-value} \propto D\,(H_{2conc.}) + C\,(OD_{340})$$

where $H_{2conc.}$ designates concentration of hydrogen in the reactor expressed in cubic centimeters of hydrogen at 1 atmosphere absolute pressure and 0° C. dissolved per gram of crude terephthalic acid feed solution, $OD_{340}$ is the optical density value of crude terephthalic acid feed solution of the reactor, D is a number in a range of from about 0.2 to about 5.75, and C is a number in a range of from about 0.4 to about 1.4.

If it is desired to modulate the concentration of hydrogen in the solution in a hydraulically full reactor directly by adjusting flow of gaseous hydrogen to the hydrogenation reactor, then in such an event hydrogen flow rate can be adjusted to provide a change in concentration of hydrogen in a range of from about 0.03 cc/g to about 0.3 c/g for a 0.1 unit change in b*-value of the product to be implemented, or in a range of about 0.015 cc/g to about 0.15 cc/g for an observed 0.1 unit change in $OD_{340}$ of feed solution to the hydrogenation reactor.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

In Examples 1 and 2 crude terephthalic acid was recovered from post-consumer polyethylene terephthalate flake containing copper phthalocyanine ($C_{32}H_{16}CuN_8$) and/or compounds derived therefrom, by depolymerization of polyethylene terephthalate resin with superheated steam in a pool of molten resins and simultaneous vaporization of the terephthalic acid and other volatile products of hydrolysis; the resulting crude terephthalic acid, which contained significantly lower levels of copper, can be purified by hydrogenation in an aqueous solution. Resulting purified terephthalic acid can, subsequently, be polyesterified to form polyethylene terephthalate resins having excellent color.

Depolymerization and Vaporization

Apparatus used in this example included a stainless steel hydrolysis vessel without mechanical means for agitating the liquid containing molten polyethylene terephthalate resin in the hydrolysis zone which cylindrical hydrolysis section of the vessel had dimensions of about 4.5 cm internal diameter and length of about 20 cm. An upper section of the vessel for disengagement of liquid from vapors formed in the lower hydrolysis zone, included a cylindrical section which had dimensions of about 9.9 cm internal diameter and length of about 15 cm and a side arm. External heating was provided for the entire vessel and side arm.

Operation of the system was started by introducing stem into the bottom of the hydrolysis vessel through a stainless steel gas dispersion frit at a rate of about 2.2 g/minute and dropping granulated waste resin into the vessel from overhead through a rotary valve until the depth of the liquid pool containing molten polyethylene terephthalate resin in the lower section of the hydrolysis vessel was about 20 cm. During a period of about 650 minutes of lined-out operation, granulated waste resin was added batch-wise to maintain the pool level and the pool temperature averaged about 345° C. A sweep of nitrogen was maintained through the upper vapor disengaging zone, side arm, and recovery apparatus which included a receiver flask and knock-back condenser.

Example 1

A commercially available waste green polyethylene terephthalate flake (682.9 g) containing about 4.1 ppm copper and about 39 ppm titanium. Typically, measurement of color level for this source of waste polyethylene terephthalate resin from green beverage bottles gave an a*-value of about −32 (green), and a b*-value of about 17 (yellow). Total weight of condensed products collected during a period of 363 minutes was 624.1 g (16.8% solids). Solids were recovered from the total product by filtration at reflux temperature with the aid of added water (592 g), and dried. This crude terephthalic acid product (94 g, 89.2% terephthalic acid, 4.0% MHET, and 0.2% BHET by L.C. analyses) was identified as Crude TA-1. Analysis of Crude TA-1 found that it contained less than 0.7 ppm of copper and about 0.7 ppm titanium. Measurement of color level for Crude TA-1 gave a L*-value of 93.6, an a*-value of 0.0, and a b*-value of 8.5.

Example 2

The procedure of Example 1 was again followed is this example. During a 285 minute run of lined-out operation, granulated waste resin was added batch-wise to maintain the pool level and the pool temperature averaged 346° C. Total weight of condensed products collected was 619.2 g (20.4% solids). Solids were recovered from the total product by filtration at reflux temperature with the aid of added water (192 g), and dried. This crude terephthalic acid product (116 g, 83.1% terephthalic acid, 4.0 MHET, and 0.2% BHET by L.C. analyses) was identified as Crude TA-2. Analysis of Crude TA-2 found that it contained less than 0.4 ppm of copper and no detectable titanium (less than 0.4 ppm). Measurement of color level for Crude TA-2 gave a L*-value of 94.8, an a*-value of-0.6, and a b*-value of 10.0.

Dark residue at the bottom of the hydrolysis vessel, collected during running of the above examples, was characterized as having weight average molecular weight of 5,540 g/mole (well below the 27,800 g/tool of the feed stock) and intrinsic viscosity of 0.09 cs (far below the 0.66 cs of feed stock). Analysis of the dark residue gave 62.21 weight percent carbon and 4.32 weight percent hydrogen which indicated that the carbon/hydrogen ratio of the residue was almost identical to that of the feed stock.

Comparative Example A

Comparative Examples A illustrates the poor color of terephthalic acid by depolymerizing waste green polyethylene terephthalate in an aqueous mixture, with and without acetic acid, at elevated temperatures and pressures which maintain the aqueous mixture in the liquid phase without separation of the terephthalic acid, ethylene glycol, and other volatile products of hydrolysis by vaporization from the reaction mixture.

A sample of waste green polyethylene terephthalate from beverage bottles, 250 lbs, in the form of ¼ inch squares was depolymerized. The sample was charged to a 250 gal stainless steel reactor with deionized water. The reactor was complete with stirring means, a thermocouple and external means for heating. After the charged reactor was purged with nitrogen, the reactor was closed and heated over a period of about 23 hours to a temperature in a range of from 240° C. to 245° C. and maintained at such temperatures for a period of about 1 hour. The reactor and resulting mixture were allowed to cool to room temperature to precipitate crude terephthalic acid. A sample of this crude terephthalic acid, identified as Comparative Example A, was then taken and analyzed for color. Comparative Example A had L*-value of 81.31, a*-value of −7.55, and b*-value of −0.63.

Example 3

In the following example crude 2,6-naphthalene dicarboxylic acid was recovered from poly(ethylene-2,6-naphthalate) resin by depolymerization of the poly(ethylene-2,6-naphthalate) resin with superheated stem and simultaneous vaporization of the 2,6-naphthalene dicarboxylic acid and other volatile products of hydrolysis.

Depolymerization and Vaporization

A vertical glass tube reactor (2 cm internal diameter) containing a porous glass frit was charged with solid poly-(ethylene-2,6-naphthalate) resin (7.0 g). Stem was pumped up through the frit, resin, side arm (about 10 cm above the frit), and into a receiver which was cooled in a water bath. As the temperature of the stem increased, the poly(ethylene-2,6-naphthalate) resin charge melted and stem bubbled up through molten resin. The stem was heated to temperatures in a range of from about 350° C. to about 360° C. Products condensed from the overhead vapor in the receiver were collected for a period of 77 minutes. White solid product (1.65 g dry) was recovered from total condensate (57 g) and was identified as Crude 2,6-NDA-1. Analysis of Crude 2,6-NDA-1 found that it contained 70.4 percent 2,6-naphthalene dicarboxylic acid. A sample of condensed solid (0.4 g) collected from the side arm upstream of the receiver contained 72.5 percent 2,6-naphthalene dicarboxylic acid.

BRIEF DESCRIPTION OF THE DRAWINGS

In the accompanying drawings forming part of the specification, in which like numerals are employed to designate like parts throughout the same.

BRIEF DESCRIPTION OF PREFERRED EMBODIMENTS

While this invention is susceptible of embodiment in many different forms, this specification and accompanying drawings disclose only some specific forms as an example of the use of the invention. In particular preferred embodiments of the invention for recovery of terephthalic acid and ethylene glycol from impure, post-consumer polyethylene terephthalate are illustrated and described. The invention is not intended to be limited to the embodiments so described, and the scope of the invention will be pointed out in the appended claims.

The apparatus of this invention is used with certain conventional components the details of which, although not fully illustrated or described, will be apparent to those having skill in the art and an understanding of the necessary function of such components.

Figure 1:
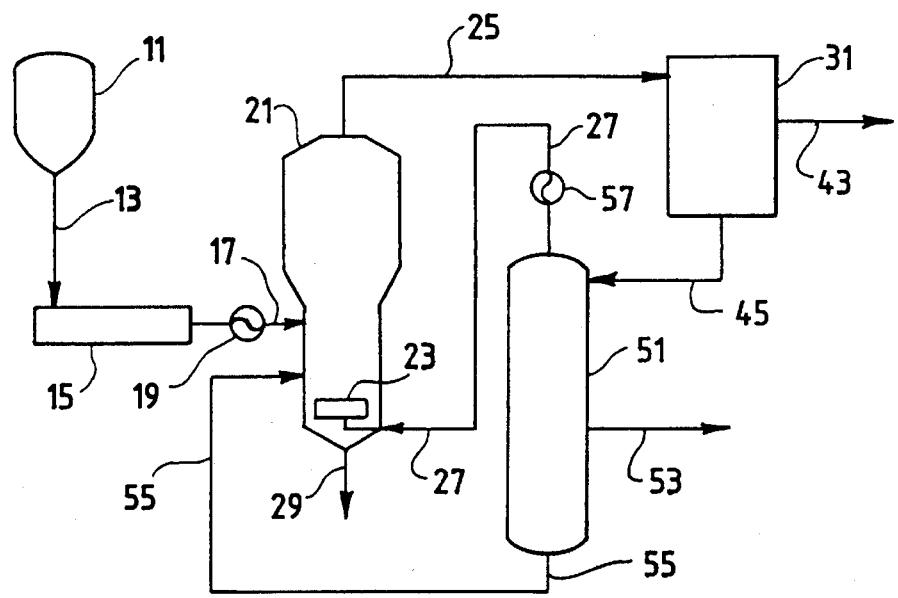
FIG. 1 is a simplified diagrammatic representation of a portion of an integrated commercial system for recovery of aromatic dicarboxylic acid from waste polyester resin and includes provisions for hydrolysis of the ester bonds and vaporization of the aromatic carboxylic acid and other volatile products of hydrolysis, introducing the materials essential for hydrolysis such as molten polyester resin and superheated stem, for receiving and condensing the products of hydrolysis, recovering crystals of the aromatic carboxylic acid from mother liquor, and separating the dihydric alcohol from water and recyclable products of hydrolysis in the mother liquor.

More specifically with reference to FIG. 1, the integrated system comprises one or more hydrolysis vessels, such as hydrolysis vessel 2 1 shown without mechanical means for agitating the liquid containing molten polyethylene terephthalate resin in the hydrolysis zone. Mechanical means for agitating the liquid, such as a stirrer may, however, be desired or needed by the particular design of hydrolysis vessel 21 and the manner in which gas containing water such as superheated stem is introduced into the hydrolysis zone. Theoretical water for hydrolysis of the ester bonds involved in completely depolymerizing polyethylene terephthalate resin is 2 moles per mole of terephthalic acid or ethylene glycol residue.

Operation of the system is started by transferring flaked waste resin from feed silo 11 by pneumatic conveyor 13 to screw extruder 15 which charges resin through preheater 19 and transfer conduit 17 discharging into the liquid pool containing molten polyethylene terephthalate resin in the hydrolysis zone of hydrolysis vessel 21. Hydrolysis vessel 21 is, advantageously, provided with means for adding external heat to the liquid pool and controlling temperatures in the lower hydrolysis zone and upper vapor disengaging zone. Superheated stem is forced into liquid near the bottom of the pool through dispersion system 23.

Depolymerization of waste resin and vaporization of ethylene glycol, terephthalic acid, and other volatile products from the hydrolysis of polyethylene terephthalate are carried out at temperatures in a range of from about 250° C. to about 400° C. and any suitable pressure, typically at pressures in a range of from about atmospheric to about 100 psig.

Less volatile and non-volatile impurities including metals, colored and color causing compounds, which are, typically, found in post-consumer polyester resins, and possibly other polymers such as polyolefins, are purged from the bottom of the pool through waste purge conduit 29.

A mixture containing ethylene glycol vapor, terephthalic acid vapor, and other volatile products of hydrolysis in the disengaging zone above the liquid pool is discharged through transfer line 25 to condenser and solids recovery unit 31. Recovered terephthalic acid product is transferred from unit 31 to storage and/or shipment by conveyor 43. Effluent liquor containing water, ethylene glycol, and mono(2-hydroxyethyl)-terephthalate is discharged from condenser and solids recovery unit 31 through conduit 45 into dehydration tower 51.

Water vapor is taken overhead from dehydration tower 51 through superheater 57 and returned to the hydrolysis zone of hydrolysis vessel 21 through conduit 27. Ethylene glycol product free of mono(2-hydroxyethyl)-terephthalate is withdrawn from dehydration tower 51 through product line 53. A bottoms effluent from dehydration tower 51, containing intermediate products from the hydrolysis such as mono(2-hydroxyethyl)-terephthalate and some ethylene glycol, is returned to the hydrolysis zone of hydrolysis vessel 21 through conduit 55.

Figure 2:
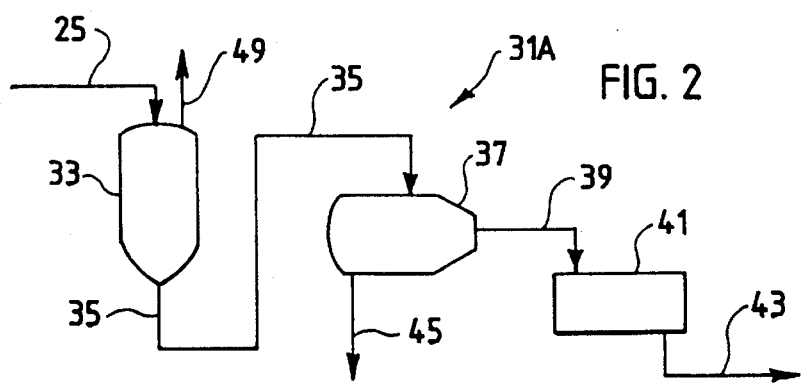
FIG. 2 illustrates diagrammatically a system for processing the vapor effluent from the hydrolysis vessel with provisions for complete condensation of the vapor effluent prior to recovering crystals of the aromatic dicarboxylic acid, separation of aromatic acid crystals from mother liquor, and a means for preparing the aromatic acid for shipment and/or use as a starting material for use in chemical reactions.

The mixture containing ethylene glycol vapor, terephthalic acid vapor, and other volatile products of hydrolysis withdrawn from the disengaging zone of hydrolysis vessel 21 through transfer line 25, is fed to overhead condenser 33 of recovery unit 31A shown in FIG. 2 were the mixture is cooled to temperatures in a range downward from about 100° C. to about 10° C. completely condensing volatile products of hydrolysis which fall into a slurry pool at the bottom of condenser 33. Any uncondensed gases and vapors are vented as is required through vent line 49. Separation of the solid phase (crystallized terephthalic acid) from the liquid phase (ethylene glycol, mono(2-hydroxyethyl)-terephthalate, and water) can be accomplished by the use of any device for accomplishing such a phase separation. For example, the phase separation can be carried out by decantation, filtration or centrifugation. Centrifugal filters, filter presses or vacuum rotary filters can be employed for recovering the crystallized terephthalic acid from the mother liquor. The slurry of terephthalic acid crystals having a solids content of from about 2 to about 20 weight percent solids, is withdrawn from the bottom of the overhead condenser 33 through conduit 35 discharging into solid-liquid separator 37 to obtain a terephthalic acid cake. Mother liquor from separator 37 is transferred through conduit 45 to dehydration tower 51. Wet cake containing from about 20 to about 60 weight percent moisture, is discharged from separator 37 through transfer line 39 to acid product dryer 41. Transfer line 39 is preferably a screw conveyor although belt or scoop conveyors can also be used in this service. Vapor from product dryer 41 is, advantageously, also fed to overhead condenser 33 along with the volatile products of hydrolysis. Dry product is conveyed by conveyor 43 to silo storage (not shown).

Figure 3:
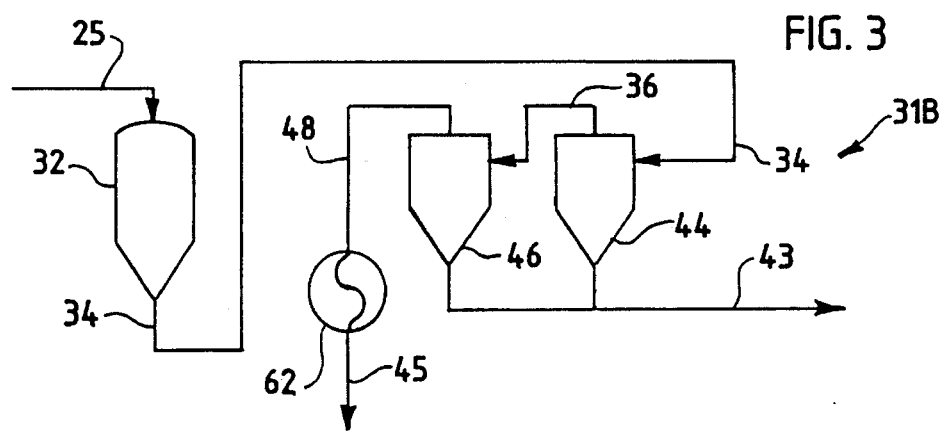
FIG. 3 illustrates diagrammatically a system for processing the vapor effluent from the hydrolysis vessel with provisions for primary partial condensation of the vapor effluent, recovery of crystals of the aromatic dicarboxylic acid, and secondary condensation of overhead vapor.

Now turning to FIG. 3, the mixture containing ethylene glycol vapor, terephthalic acid vapor, and other volatile products of hydrolysis withdrawn from the disengaging zone of hydrolysis vessel 21 through transfer line 25, is fed to primary direct contact condenser 32 of recovery unit 31B were cool make up water is sprayed into the mixture partially condensing the vapors. The mixture is cooled down to temperatures in a range of from about 150° C. to about 250° C. at a pressure in a range from about 0 to about 100 psig. These conditions are, typically, optimized such that more than 95 mole percent of the terephthalic acid is precipitated, leaving ethylene glycol, mono(2-hydroxyethyl)-terephthalate, and water completely in the gas phase. The resulting gas-solid mixture is withdrawn from primary condenser 32 through transfer conduit 34 and fed to product cyclone separator 44 where terephthalic acid precipitate is separated from overhead vapor which, is fed to product cyclone separator 46 through transfer conduit 36. Recovered terephthalic acid precipitate from both cyclone separators is conveyed by conveyor 43 to silo storage (not shown). Overhead vapor from product cyclone separator 46 is transferred through overhead vapor line 48 to secondary condenser 62 where overhead vapor is cooled to temperatures in a range downward from about 100° C. to about 10° C. form a liquor of completely condensing volatile products. The liquor from secondary condenser 62 is transferred through conduit 45 to dehydration tower 51.

That which is claimed is:

1. A process for preparation of aromatic acid vapors and dihydric alcohol vapors from polyester resins comprising repeating units of dibasic aromatic acid residue and repeating units of dihydric alcohol residue linked by ester bonds, which process comprises: treating the polyester resins with excess superheated stem in a pool containing molten resins, and continuously removing therefrom a mixture of vapors containing aromatic acid, dihydric alcohol, other volatile products of hydrolysis of the ester bonds, and water in an mount of at least about 2 moles of water per mole of aromatic acid in the mixture of vapors.

2. The process according to claim 1 wherein the dibasic aromatic acid is at least one member of the group consisting of isophthalic acid, terephthalic acid, and 2,6-naphthalene dicarboxylic acid.

3. The process according to claim 1 wherein polyethylene terephthalate resins are treated with excess superheated stem at temperatures in a rage of from about 250° C. to about 450° C.

4. The process according to claim 1 wherein poly( ethylene-2,6-naphthalate) resins are treated with excess superheated stem at temperatures in a range of from about 250° C. to about 450° C.

5. A process for recovering dibasic aromatic acid and dihydric alcohol from polyester resin comprising repeating units of dibasic aromatic acid residue and repeating units of dihydric alcohol residue linked by ester bonds which process comprises:

depolymerizing polyester resin in a molten polyester resin containing solvent under conditions suitable for hydrolysis of ester bonds to form a reaction mixture containing aromatic acid, dihydric alcohol, impurities and other components of the resin;

vaporizing from the reaction mixture the aromatic carboxylic acid, dihydric alcohol, and other volatile products of hydrolysis with excess superheated stem to obtain a continuous effluent of depolymerization comprising aromatic acid, dihydric alcohol, and other volatile products of hydrolysis, and water in an amount of at least about 2 moles of water per mole of aromatic acid in the mixture of vapors; and separating from the effluent of depolymerization a solid product of crude dibasic aromatic acid substantially free of dihydric alcohol, but containing organic impurities, to form a residue containing dihydric alcohol.

6. The process according to claim 5 wherein the dibasic aromatic acid is at least one member of the group consisting of isophthalic acid, terephthalic acid, and 2,6-naphthalene dicarboxylic acid.

7. The process according to claim 5 wherein the process further comprises:

fractionating at least a portion of a residue resulting from the separation of aromatic acid from the effluent of depolymerization to obtain a dihydric alcohol product substantially free of lower boiling compounds.

8. The process according to claim 5 wherein both the depolymerization of polyester resin and the vaporization of the aromatic carboxylic acid and other volatile products of hydrolysis, are carried out together in one or more reaction zones.

9. The process according to claim 8 wherein polyethylene terephthalate resins are treated with excess superheated stem at temperatures in a range of from about 250° C. to about 450° C. and pressures sufficient to maintain a molten phase.

10. The process according to claim 8 wherein poly(ethylene-2,6-naphthalate) resins are treated with excess superheated stem at temperatures in a rage of from about 250° C. to about 450° C. and pressures sufficient to maintain a molten phase.

11. The process according to claim 8 wherein the process further comprises:

fractionating at least a portion of a residue resulting from the separation of aromatic acid from the effluent of depolymerization to obtain a dihydric alcohol product fraction substantially free of lower boiling compounds and a fraction containing lower boiling compounds; and wherein the depolymerization of polyester resin is carried out in the presence of at least a portion of the fraction containing lower boiling compounds in one or more of the reaction zones.

12. The process according to claim 5 wherein the process further comprises:

reduction of at least a portion of the organic impurities in the crude dibasic aromatic acid in an aqueous solution at elevated temperatures and pressures and in the presence of hydrogen and at least one insoluble Group VIII noble metal-containing catalyst;

separating the solid noble metal-containing catalyst from the aqueous solution; and crystallizing and separating purified dibasic aromatic acid from the aqueous solution.

13. The process according to claim 12 wherein the dibasic aromatic acid is terephthalic acid, the noble metal is at least one member of the group consisting of palladium and rhodium, and the purified dibasic aromatic acid has a total metals content of less than 100 ppm and contains less than 1000 ppm total of 4-carboxybenzaldehyde and toluic acid.

14. A process for recovering terephthalic acid from polyethylene terephthalate resin comprising repeating units of terephthalic acid residue and repeating units of ethylene glycol residue linked by ester bonds which process comprises:

depolymerizing polyethylene terephthalate resin with excess superheated stem in a pool containing molten resins under conditions suitable for hydrolysis of ester bonds to form a reaction mixture containing terephthalic acid, ethylene glycol, impurities and other components of the resins;

vaporizing from the reaction mixture the terephthalic acid, ethylene glycol, and other volatile products of hydrolysis with excess superheated stem to obtain a continuous effluent of depolymerization comprising terephthalic acid, ethylene glycol, other volatile products of hydrolysis, and water in an mount of at least about 2 moles of water per mole of terephthalic acid in the effluent of depolymerization;

separating from the effluent of depolymerization a, solid product of crude terephthalic acid substantially free of ethylene glycol, but containing organic impurities, to form an aqueous residue containing ethylene glycol; and fractionating at least a portion of the aqueous residue to obtain dehydrated ethylene glycol substantially free of lower boiling compounds, and a fraction containing lower boiling compounds.

15. The process according to claim 14 wherein the depolymerization of polyester resin is carried out in the presence of at least a portion of the fraction containing lower boiling compounds in one or more of the reaction zones.

16. The process according to claim 14 wherein the process further comprises:

reducing at least a portion of the organic impurities in the crude terephthalic acid in an aqueous solution at elevated temperatures and pressures and in the presence of hydrogen and an insoluble catalyst containing a palladium component on a carbon support;

separating the insoluble catalyst from the aqueous solution; and crystallizing and separating purified terephthalic acid from the aqueous solution while maintaining the temperature in a rage of from about 50° C. to about 150° C.

17. The process according to claim 16 wherein the resulting purified terephthalic acid has a L*-value in a range of from about 95 to about 100, an a*-value in a rage of from about −1 to about +1, and a b*-value in a rage of from about 0.5 to about 2.

18. A process for recovering 2,6-naphthalene dicarboxylic acid from poly(ethylene-2,6-naphthalate) resin comprising repeating units of 2,6-naphthalene dicarboxylic acid residue and repeating units of ethylene glycol residue linked by ester bonds which process comprises:

depolymerizing from poly(ethylene-2,6-naphthalate) resin with excess superheated steam in a pool containing molten resins under conditions suitable for hydrolysis of ester bonds to form a reaction mixture containing 2,6-naphthalene dicarboxylic acid, ethylene glycol, impurities and other components of the resins;

vaporizing from the reaction mixture the 2,6-naphthalene dicarboxylic acid, ethylene glycol, and other volatile products of hydrolysis with excess superheated steam to obtain a continuous effluent of depolymerization comprising 2,6-naphthalene dicarboxylic acid, ethylene glycol, other volatile products of hydrolysis, and water in an amount of at least about 2 moles of water per mole of 2,6-naphthalene dicarboxylic acid in the effluent of depolymerization;

separating from the effluent of depolymerization a solid product of crude 2,6-naphthalene dicarboxylic acid substantially free of ethylene glycol, but containing organic impurities, to form an aqueous residue containing ethylene glycol; and fractionating at least a portion of the aqueous residue to obtain dehydrated ethylene glycol substantially free of lower boiling compounds, and a fraction containing lower boiling compounds:

wherein the depolymerization of poly(ethylene-2,6-naphthalate) resin is carried out in the presence of at least a portion of the fraction containing lower boiling compounds in one or more of the reaction zones.

19. The process according to claim 18 wherein the process further comprises:

reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst; separating the insoluble catalyst from the aqueous solution; and crystallizing and separating purified 2,6-naphthalene dicarboxylic acid from the aqueous solution while maintaining the temperature in a range of from about 50° C. to about 250° C.

20. The process according to claim 18 wherein the purified 2,6-naphthalene dicarboxylic acid has an optical density in a range from about 0 to about 5, an ash content of less 200 ppm, while maintaining the aqueous solution during the reduction at temperatures in a range of from about 100° C. to about 250° C.

* * * * *

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

On title page, item [56], lines 5-6 in the "ABSTRACT" patent reads "molten polyester resin containing solvent with superheated stem," patent should read --molten polyester resin containing solvent with superheated steam,-- lines 21 - 22 in the "ABSTRACT" patent reads "an a*-value in a rage of from about -1 to about +1," patent should read --an a*-value in a range of from about -1 to about +1,--

Col. 1 lines 27-28 "superheated stem" should read --superheated steam--

Col. 1 line 45 "superheated stem" should read --superheated steam--

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

| Col. | Line |   |
|------|------|---|
| 4 | 22-23 | "superheated stem" should read --superheated steam-- |
| 5 | 2 | "superheated stem" should read --superheated steam-- |
| 6 | 6-7 | "water in an mount of at least about 2 moles of water per mole of terephthalic acid" should read --water in an amount of at least about 2 moles of water per mole of terephthalic acid-- |
| 6 | 32-33 | "superheated stem" should read --superheated steam-- |
| 6 | 39 | "superheated stem" should read --superheated steam-- |
| 6 | 42 | "water in an mount" should read --water in an amount-- |

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

| Col. | Line | |
|---|---|---|
| 7 | 56-57 | "polyester that is mixed witch other plastics." should read --polyester that is mixed with other plastics.-- |
| 7 | 60 | "metal-organic components" should read --metallo-organic components-- |
| 8 | 19 | "Excess stem" should read --Excess steam-- |
| 8 | 63-64 | "the purification step can he operated in several modes." should read --the purification step can be operated in several modes.-- |
| 10 | 32-33 | " "11766 Rhodium, 1 % on Stem Activated Carbon Granules, Anhydrous." " should read -- "11766 Rhodium, 1 % on Steam Activated Carbon Granules, Anhydrous." -- |

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

| Col. | Line | | |
|---|---|---|---|
| 13 | 9 | "stem" should read | --steam-- |
| 13 | 53 | "4.0 MHET," should read | --4.0% MHET,-- |
| 13 | 62 | "27,800 g/tool" should read | --27,800 g/mol-- |
| 14 | 16-17 | "heated over a period of about 23 hours" should read | --heated over a period of about 3 hours-- |
| 14 | 31 | "superheated stem" should read | --superheated steam-- |
| 14 | 39 | "Stem was pumped" should read | --Steam was pumped-- |
| 14 | 42 | "stem" should read | --steam-- |

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

| Col. | Line | |
|---|---|---|
| 14 | 43 | "stem bubbled up" should read --steam bubbled up-- |
| 14 | 44 | "The stem was heated" should read --The steam was heated-- |
| 14 | 67 | "superheated stem," should read --superheated steam,-- |
| 15 | 46 | "superheated stem" should read -- superheated steam -- |
| 15 | 60 | "Superheated stem" should read --Superheated steam-- |
| 17 | 26 | "superheated stem" should read --superheated steam-- |
| 17 | 37-38 | "superheated stem at temperatures in a rage of from about 250°C." should read --superheated steam at temperatures in a range of from about 250°C.-- |

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

| Col. | Line | |
|---|---|---|
| 17 | 42-43 | "superheated stem" should read --superheated steam-- |
| 17 | 57 | "superheated stem" should read --superheated steam-- |
| 18 | 16 | "superheated stem" should read --superheatd steam-- |
| 18 | 20-21 | "superheated stem at temperatures in a rage" should read --superheated steam at temperatures in a range-- |
| 18 | 67 | "superheated stem" should read --superheated steam-- |
| 19 | 30-31 | "maintaining the temperature in a rage" should read --maintaining the temperature in a range-- |
| 19 | 35 | "an a*-value in a rage" should read --an a*-value in a range-- |

UNITED STATES PATENT AND TRADEMARK OFFICE
CERTIFICATE OF CORRECTION

PATENT NO.: 5,473,102

DATED: December 5, 1995

INVENTOR(S): Floyd Johnson, David L. Sikkenga, Kalpana Danawala, Bruce I. Rosen

It is certified that error appears in the above-identified patent and that said Letters Patent is hereby corrected as shown below:

| Col. | Line | |
|---|---|---|
| 19 | 36 | "and a b*-value in a rage" should read --and a b*-value in a range-- |

Signed and Sealed this

Thirtieth Day of April, 1996

Attest:

BRUCE LEHMAN

Attesting Officer

Commissioner of Patents and Trademarks